United States Patent
Hwang et al.

(10) Patent No.: US 10,934,558 B2
(45) Date of Patent: Mar. 2, 2021

(54) RECOMBINANT VECTOR CARRYING CELLULOSE BINDING DOMAIN AND METHOD FOR ISOLATING AND PURIFYING PROTEIN, USING SAME VECTOR

(71) Applicant: BIOAPPLICATIONS INC., Gyeongsangbuk-do (KR)

(72) Inventors: Inhwan Hwang, Gyeongsangbuk-do (KR); Eun Ju Sohn, Gyeongsangbuk-do (KR); Yongjik Lee, Gyeongsangbuk-do (KR)

(73) Assignee: BIOAPPLICATIONS INC.

( * ) Notice: Subject to any disclaimer, the term of this patent is extended or adjusted under 35 U.S.C. 154(b) by 0 days.

(21) Appl. No.: 16/611,966

(22) PCT Filed: May 10, 2018

(86) PCT No.: PCT/KR2018/005371
§ 371 (c)(1),
(2) Date: Nov. 8, 2019

(87) PCT Pub. No.: WO2018/208099
PCT Pub. Date: Nov. 15, 2018

(65) Prior Publication Data
US 2020/0270624 A1    Aug. 27, 2020

(30) Foreign Application Priority Data
May 11, 2017  (KR) .................. 10-2017-0058882

(51) Int. Cl.
| | | |
|---|---|---|
| *C12N 15/82* | (2006.01) | |
| *C07K 1/22* | (2006.01) | |
| *C07K 1/30* | (2006.01) | |
| *C07K 5/11* | (2006.01) | |
| *C07K 14/195* | (2006.01) | |
| *C07K 16/00* | (2006.01) | |
| *C07K 14/35* | (2006.01) | |

(52) U.S. Cl.
CPC ............ *C12N 15/8257* (2013.01); *C07K 1/22* (2013.01); *C07K 1/30* (2013.01); *C07K 5/1019* (2013.01); *C07K 14/195* (2013.01); *C07K 16/00* (2013.01); *C12N 15/8205* (2013.01); *C07K 2319/20* (2013.01); *C07K 2319/50* (2013.01)

(58) Field of Classification Search
None
See application file for complete search history.

(56) References Cited

FOREIGN PATENT DOCUMENTS

| | | |
|---|---|---|
| JP | 11225763 A | 8/1999 |
| KR | 1020050040601 A | 5/2005 |
| KR | 100618563 B1 | 8/2006 |
| KR | 1020130130563 A | 12/2013 |
| KR | 20140044656 A | 4/2014 |
| KR | 101848082 B1 | 4/2018 |

OTHER PUBLICATIONS

GenBank Accession No. HQ232851.1; Appl. Microbiol. Biotechnol. 91 (3), 789-798 (2011).

*Primary Examiner* — Suzanne M Noakes
*Assistant Examiner* — Jae W Lee
(74) *Attorney, Agent, or Firm* — Riverside Law LLP

(57) ABSTRACT

The present invention relates to a recombinant vector carrying cellulose-binding domain 3 and a method for separating a target protein using the recombinant vector. The protein isolating method of the present invention can easily separate a fusion protein containing a target protein by using the recombinant vector to bind a transformed plant body to cellulose and can effectively isolate the target protein from a cellulose-binding domain by treating the fusion protein with enterokinase, thus being expected to find industrial applications in various fields.

15 Claims, 4 Drawing Sheets
Specification includes a Sequence Listing.

ID NO: 1, which encodes cellulose-

SEQUENCE LISTING

<160> NUMBER OF SEQ ID NOS: 8

<210> SEQ ID NO 1

-continued

<211> LENGTH: 477
<212> TYPE: DNA
<213> ORGANISM: Artificial Sequence
<220> FEATURE:
<223> OTHER INFORMATION: CBM3

<400> SEQUENCE: 1

| | | |
|---|---|---|
| gtatcaggta accttaaggt ggagttttac aactcgaacc cttctgatac aactaactca | 60 |
| ataaacccac agttcaaagt tacaaacaca ggcagctctg cgatcgattt gtctaaatta | 120 |
| accctcagat actattatac ggttgatgga cagaaggacc agactttctg gtgtgatcat | 180 |
| gcagctatca ttggttctaa cggtagctac aacggaatta catcaaacgt gaagggcact | 240 |
| ttcgttaaga tgtcctctag cactaacaac gcagacacat atttggagat cagttttacg | 300 |
| gggggaaccc ttgaaccagg tgctcacgtc cagattcaag gaagattcgc taaaaacgac | 360 |
| tggtcgaact atacccaaag taatgattac agttttaaat ccgcctcaca atttgttgag | 420 |
| tgggatcagg tcactgctta cctgaacggg gttctagtgt ggggaaagga acctggt | 477 |

<210> SEQ ID NO 2
<211> LENGTH: 159
<212> TYPE: PRT
<213> ORGANISM: Artificial Sequence
<220> FEATURE:
<223> OTHER INFORMATION: CBM3 (Amino Acid)

<400> SEQUENCE: 2

Val Ser Gly Asn Leu Lys Val Glu Phe Tyr Asn Ser Asn Pro Ser Asp
1               5                   10                  15

Thr Thr Asn Ser Ile Asn Pro Gln Phe Lys Val Thr Asn Thr Gly Ser
            20                  25                  30

Ser Ala Ile Asp Leu Ser Lys Leu Thr Leu Arg Tyr Tyr Tyr Thr Val
        35                  40                  45

Asp Gly Gln Lys Asp Gln Thr Phe Trp Cys Asp His Ala Ala Ile Ile
    50                  55                  60

Gly Ser Asn Gly Ser Tyr Asn Gly Ile Thr Ser Asn Val Lys Gly Thr
65                  70                  75                  80

Phe Val Lys Met Ser Ser Ser Thr Asn Asn Ala Asp Thr Tyr Leu Glu
                85                  90                  95

Ile Ser Phe Thr Gly Gly Thr Leu Glu Pro Gly Ala His Val Gln Ile
            100                 105                 110

Gln Gly Arg Phe Ala Lys Asn Asp Trp Ser Asn Tyr Thr Gln Ser Asn
        115                 120                 125

Asp Tyr Ser Phe Lys Ser Ala Ser Gln Phe Val Glu Trp Asp Gln Val
    130                 135                 140

Thr Ala Tyr Leu Asn Gly Val Leu Val Trp Gly Lys Glu Pro Gly
145                 150                 155

<210> SEQ ID NO 3
<211> LENGTH: 903
<212> TYPE: DNA
<213> ORGANISM: Artificial Sequence
<220> FEATURE:
<223> OTHER INFORMATION: Ag85A

<400> SEQUENCE: 3

| | | |
|---|---|---|
| tttagccggc ctggcctgcc tgtggaatac ctgcaggtgc ctagccctag catgggccgg | 60 |
| gacatcaaag tgcagtttca gagcggcggg gctaatagcc ctgctctgta cctgctcgat | 120 |
| ggcctgcggg ctcaggatga ttttagcggc tgggacatca cacccctgc ttttgaatgg | 180 |

-continued

```
tacgatcaga gcggcctgag cgtcgtgatg cctgtgggcg ggcagagcag cttctacagc    240
gattggtatc agcctgcttg cggcaaagct ggctgccaga cctacaagtg ggaaaccttt    300
ctgaccagcg aactgcctgg ctggctgcag gctaatcggc acgtgaaacc taccggcagc    360
gccgtggtgg gcctgagcat ggctgctagc tccgctctga ccctggctat ctaccaccct    420
cagcagtttg tgtacgctgg cgctatgagc ggcctgctcg atccctccca ggctatgggc    480
cctaccctga tcgggctcgc tatgggggat gctgggggt acaaagctag cgatatgtgg     540
ggccctaaag aagatcctgc ttggcagcgg aatgatcctc tgctcaacgt gggcaaactg    600
atcgctaata taccgagt gtgggtgtac tgcggcaatg gcaaacctag cgatctgggc      660
gggaacaatc tgcctgctaa atttctggaa ggcttcgtgc ggaccagcaa catcaagttt    720
caggatgctt acaatgctgg cggggggccac aatggcgtat ttgattttcc tgatagcggc   780
acccacagct gggaatactg gggcgctcag ctgaatgcta tgaaacctga tctgcagcgg    840
gctctgggcg ctacccctaa taccggcccct gctcctcagg gcgctggctc cggatctggt   900
agt                                                                  903
```

<210> SEQ ID NO 4
<211> LENGTH: 301
<212> TYPE: PRT
<213> ORGANISM: Artificial Sequence
<220> FEATURE:
<223> OTHER INFORMATION: Ag85A (Amino Acid)

<400> SEQUENCE: 4

```
Phe Ser Arg Pro Gly Leu Pro Val Glu Tyr Leu Gln Val Pro Ser Pro
1               5                   10                  15

Ser Met Gly Arg Asp Ile Lys Val Gln Phe Gln Ser Gly Gly Ala Asn
            20                  25                  30

Ser Pro Ala Leu Tyr Leu Leu Asp Gly Leu Arg Ala Gln Asp Asp Phe
        35                  40                  45

Ser Gly Trp Asp Ile Asn Thr Pro Ala Phe Glu Trp Tyr Asp Gln Ser
    50                  55                  60

Gly Leu Ser Val Val Met Pro Val Gly Gly Gln Ser Ser Phe Tyr Ser
65                  70                  75                  80

Asp Trp Tyr Gln Pro Ala Cys Gly Lys Ala Gly Cys Gln Thr Tyr Lys
                85                  90                  95

Trp Glu Thr Phe Leu Thr Ser Glu Leu Pro Gly Trp Leu Gln Ala Asn
            100                 105                 110

Arg His Val Lys Pro Thr Gly Ser Ala Val Val Gly Leu Ser Met Ala
        115                 120                 125

Ala Ser Ser Ala Leu Thr Leu Ala Ile Tyr His Pro Gln Gln Phe Val
    130                 135                 140

Tyr Ala Gly Ala Met Ser Gly Leu Leu Asp Pro Ser Gln Ala Met Gly
145                 150                 155                 160

Pro Thr Leu Ile Gly Leu Ala Met Gly Asp Ala Gly Gly Tyr Lys Ala
                165                 170                 175

Ser Asp Met Trp Gly Pro Lys Glu Asp Pro Ala Trp Gln Arg Asn Asp
            180                 185                 190

Pro Leu Leu Asn Val Gly Lys Leu Ile Ala Asn Asn Thr Arg Val Trp
        195                 200                 205

Val Tyr Cys Gly Asn Gly Lys Pro Ser Asp Leu Gly Gly Asn Asn Leu
    210                 215                 220
```

```
Pro Ala Lys Phe Leu Glu Gly Phe Val Arg Thr Ser Asn Ile Lys Phe
225                 230                 235                 240

Gln Asp Ala Tyr Asn Ala Gly Gly Gly His Asn Gly Val Phe Asp Phe
                245                 250                 255

Pro Asp Ser Gly Thr His Ser Trp Glu Tyr Trp Gly Ala Gln Leu Asn
                260                 265                 270

Ala Met Lys Pro Asp Leu Gln Arg Ala Leu Gly Ala Thr Pro Asn Thr
        275                 280                 285

Gly Pro Ala Pro Gln Gly Ala Gly Ser Gly Ser Gly Ser
    290                 295                 300

<210> SEQ ID NO 5
<211> LENGTH: 30
<212> TYPE: DNA
<213> ORGANISM: Artificial Sequence
<220> FEATURE:
<223> OTHER INFORMATION: Linker

<400> SEQUENCE: 5
gaggcagccg ctaaggaagc tgcagcgaaa                                    30

<210> SEQ ID NO 6
<211> LENGTH: 15
<212> TYPE: DNA
<213> ORGANISM: Artificial Sequence
<220> FEATURE:
<223> OTHER INFORMATION: EK

<400> SEQUENCE: 6
gatgacgacg ataaa                                                    15

<210> SEQ ID NO 7
<211> LENGTH: 272
<212> TYPE: DNA
<213> ORGANISM: Artificial Sequence
<220> FEATURE:
<223> OTHER INFORMATION: BiP

<400> SEQUENCE: 7
atggctcgct cgtttggagc taacagtacc gttgtgttgg cgatcatctt cttcggtgag    60
tgattttccg atcttcttct ccgatttaga tctcctctac attgttgctt aatctcagaa   120
ccttttttcg ttgttcctgg atctgaatgt gtttgtttgc aatttcacga tcttaaaagg   180
ttagatctcg attggtattg acgattggaa tctttacgat ttcaggatgt ttatttgcgt   240
tgtcctctgc aatagaagag gctacgaagt ta                                 272

<210> SEQ ID NO 8
<211> LENGTH: 4
<212> TYPE: PRT
<213> ORGANISM: Artificial Sequence
<220> FEATURE:
<223> OTHER INFORMATION: HDEL (Amino Acid)

<400> SEQUENCE: 8

His Asp Glu Leu
1
```

RECOMBINANT VECTOR CARRYING CELLULOSE BINDING DOMAIN AND METHOD FOR ISOLATING AND PURIFYING PROTEIN, USING SAME VECTOR

CROSS-REFERENCE TO RELATED APPLICATIONS

This application is the U.S. national phase application filed under 35 U.S.C. § 371 claiming benefit to International Patent Application No. PCT/KR2018/005371, filed on May 10, 2018, which is entitled to priority under to Korean Patent Application No. 10-2017-0058882, filed May 11, 2017, the disclosure of which is incorporated herein by reference in their entireties.

TECHNICAL FIELD

The present invention relates to a recombinant vector carrying a cellulose-binding domain, and a method of isolating and purifying a protein using the vector.

BACKGROUND ART

Cellulose is a type of organic compound which accounts for about 30% or more of a plant body as an essential constituent of the cell membrane and the xylem of a plant. Cellulose is a type of polysaccharide, its chemical structure is formed by polymerizing D-glucose by β-1,4-glycosidic bonds, and the molecular weight of a natural state is tens to hundreds of thousands. Cellulose is an odorless white solid, not dissolved in water, ethanol or ether, and has considerably strong resistance to an alkaline, but is hydrolyzed in an acid or a copper ammonia solution, thereby mass-producing cellobiose as an intermediate, and finally being converted into glucose.

Cellulose is one type of the most abundant natural resources in nature, and various studies of utilizing cellulose are progressing.

Meanwhile, cellulase for degrading cellulose has a cellulose-binding domain (CBD), and specifically binds to cellulose and thus effectively degrades cellulose. Attempts have been widely made to produce a recombinant protein that specifically binds to cellulose by binding to a target protein requiring cellulose-binding domain as described above (Korean Patent No. 10-0618563). However, these attempts are limited to methods of preparing a recombinant protein using a microorganism, and examples using plants have not been known yet.

However, recently, as interest has been focused on the production of plant-derived recombinant proteins and vaccines, there is an urgent need to develop a method of producing a large amount of recombinant protein using a plant body, and rapidly and cheaply isolating a high purity recombinant protein in a large amount.

DISCLOSURE

Technical Problem

The present invention is provided to solve the conventional technical problems described above, and to produce a target protein in a plant body and then rapidly and simply isolate the produced target protein in a large amount, the present invention is directed to providing a recombinant vector carrying cellulose-binding module 3 (CBM3), and a method of isolating and purifying target protein using the recombinant vector.

However, technical problems to be solved in the present invention are not limited to the above-described issues, and other issues which are not described herein will be fully understood by those of ordinary skill in the art from the following descriptions.

Technical Solution

To achieve the object of the present invention, the present invention provides a recombinant vector comprising a base sequence of SEQ ID NO: 1, which encodes cellulose-binding module 3, and the configuration of the recombinant vector is shown in FIG. 1.

In one exemplary embodiment of the present invention, in the recombinant vector, cellulose-binding module 3, a linker peptide, an enterokinase-cleavage site, and a target protein-encoding gene may be sequentially connected.

In another exemplary embodiment of the present invention, the target protein-encoding gene may consist of a base sequence of SEQ ID NO: 3.

In still another exemplary embodiment of the present invention, the linker peptide may consist of a base sequence of SEQ ID NO: 5.

In yet another exemplary embodiment of the present invention, the enterokinase-cleavage site may consist of a base sequence of SEQ ID NO: 6.

In yet another exemplary embodiment of the present invention, a binding immunoglobulin protein (BiP)-encoding gene, which can transfer a target protein to the endoplasmic reticulum in plant cells may further be operably linked to the recombinant vector.

In yet another exemplary embodiment of the present invention, the BiP-encoding gene may consist of a base sequence of SEQ ID NO: 7.

In yet another exemplary embodiment of the present invention, a base sequence encoding a His-Asp-Glu-Leu (HDEL) peptide may further be operably linked to the recombinant vector.

In addition, the present invention provides a method of isolating and purifying a target protein, which comprises the following steps:

preparing a plant body mixed solution by mixing a plant body transformed using the recombinant vector with a protein extraction buffer solution (S1);

adsorbing a fusion protein, in which cellulose-binding module 3 and a target protein are fused, to cellulose by injecting the mixed solution of S1 into a column filled with cellulose (S2); and obtaining a suspension by precipitating the fusion protein-adsorbed cellulose in S2 through centrifugation and suspending the precipitate in enterokinase (S3).

In one exemplary embodiment of the present invention, after S3, removing enterokinase by injecting the suspension into a sepharose column may be further comprised.

In another exemplary embodiment of the present invention, the protein extraction buffer solution may comprise a 10 to 100 mM Tris buffer solution, a 100 to 200 mM sodium chloride (NaCl) solution, 0.01 to 0.5% Triton X-100, and a protease inhibitor.

In still another exemplary embodiment of the present invention, the transformed plant body may be prepared by:

a) making a transformant by introducing the recombinant vector to a strain; and b) transforming a plant body using the transformant.

In yet another exemplary embodiment of the present invention, the strain may be *Agrobacterium tumefaciens*.

In yet another exemplary embodiment of the present invention, the plant body may be a dicotyledonous plant selected from the group consisting of *Arabidopsis thaliana*, soybean, tobacco, eggplant, pepper, potato, tomato, Chinese cabbage, radish, cabbage, lettuce, peach, pear, strawberry, watermelon, melon, cucumber, carrot and celery; or a monocotyledonous plant selected from the group consisting of rice, barley, wheat, lye, corn, sugarcane, oat and onion.

In yet another exemplary embodiment of the present invention, the cellulose may be microcrystalline cellulose.

Advantageous Effects

A method of isolating a protein using a recombinant vector of the present invention can rapidly isolate a desired protein with high purity from a total extract of a plant body in which various proteins are mixed, and isolate an even low concentration of a protein by preventing binding of non-specific proteins using cellulose-binding module 3 having high affinity to cellulose. In addition, the target protein and the protein-tagged cellulose-binding domain can be treated with enterokinase, thereby rapidly isolating the target protein. Therefore, since the method of isolating a protein of the present invention can quickly, cheaply, and effectively separate a large amount of target protein from a plant body with high purity, it is expected to be applied to various industrial fields.

MODES OF THE INVENTION

Figure 1:
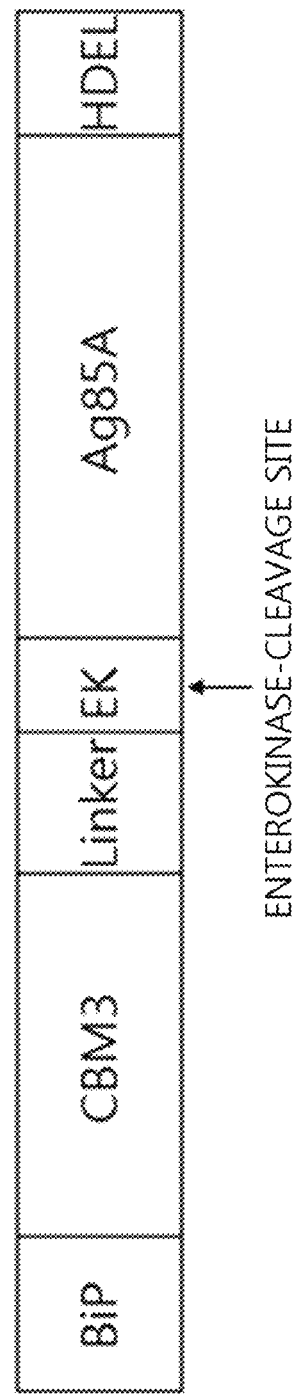
FIG. 1 illustrates the configuration of a recombinant vector used in the present invention.

The present invention is characterized by providing a recombinant vector comprising a base sequence of SEQ ID NO: 1, which encodes cellulose-binding module 3 (CBM3).

As a result of studying a method of rapidly and cheaply isolating a high purity target protein from a plant body in a large amount, the invention was completed. That is, in an exemplary embodiment of the present invention, it was confirmed that a target protein could be isolated by manufacturing a recombinant vector by binding cellulose-binding module 3 (CBM3) consisting of a base sequence of SEQ ID NO: 1 or an amino acid sequence of SEQ ID NO: 2 in the direction of the 3' end of the target protein-encoding gene, preparing a transformed plant body producing the target protein using the recombinant vector, isolating a CBM3 fusion protein using microcrystalline cellulose (MCC), and treating the resulting protein with enterokinase (refer to Examples 1 to 4).

From a result of the above, the inventors knew that a target protein could be efficiently purified using cellulose from a plant body expressing the target protein using a recombinant vector carrying cellulose-binding domain.

Accordingly, the present invention may provide a method of isolating a target protein using the recombinant vector.

Therefore, the present invention provides a method of isolating and purifying a target protein, which comprises the following steps:

preparing a plant body mixed solution by mixing a plant body transformed using the recombinant vector with a protein extraction buffer solution (S1);

adsorbing a fusion protein, in which cellulose-binding module 3 and a target protein are fused, to cellulose by injecting the mixed solution of S1 into a column filled with cellulose (S2); and obtaining a suspension by precipitating the fusion protein-adsorbed cellulose in S2 through centrifugation and suspending the precipitate in enterokinase (S3).

More specifically, in the present invention, the cellulose preferably uses MCC. Amorphous cellulose may also be used, but MCC is more preferably used in consideration of isolation efficiency.

In the present invention, the recombinant vector consists of cellulose-binding module 3, a linker peptide, an enterokinase-cleavage site, and a target protein-encoding gene, which is sequentially connected, a signal peptide of a binding immunoglobulin protein (BiP) which can transfer a target protein to an endoplasmic reticulum in plant cells is connected to the 3' end of cellulose-binding domain, and His-Asp-Glu-Leu (HDEL) may be connected to a carboxyl end of the target protein-encoding gene so that the connected vector is retained in the endoplasmic reticulum. The cellulose-binding module 3 may be encoded by a base sequence of SEQ ID NO: 1. In a protein produced using the recombinant vector, cellulose-binding module 3 consists of an amino acid sequence of SEQ ID NO: 2.

The term "target protein (or protein)" used herein refers to a protein to be produced by a genetic engineering method according to the present invention, and the present invention is not particularly limited thereto. Preferably, proteins required to be mass-produced may be included since they are used industrially.

In an exemplary embodiment of the present invention, although the target protein-encoding gene may be Ag85A encoded by a base sequence of SEQ ID NO: 3, it may be isolated as described above, and vary according to the type of desired protein to be produced. The target protein may consist of an amino acid sequence of SEQ ID NO: 4.

In another exemplary embodiment of the present invention, the linker peptide may consist of a base sequence of SEQ ID NO: 5, the enterokinase-cleavage site may consist of a base sequence of SEQ ID NO: 6, and the signal peptide of BiP may consist of a base sequence of SEQ ID NO: 7.

The term "fusion protein" used herein refers to a protein in which cellulose-binding domain and a target protein are fused, and in the fusion protein, the removal of cellulose-binding domain corresponding to a tag from a target protein is critical for isolation and purification of the target protein. Therefore, in the present invention, cellulose-binding domain may be easily isolated by the treatment of enterokinase.

In still another exemplary embodiment of the present invention, after the treatment with enterokinase, the enterokinase may be easily removed by being passed through a sepharose column (STI-sepharose affinity chromatography).

In yet another exemplary embodiment of the present invention, a protein extraction buffer solution added to prepare a plant body mixed solution may comprise a 10 to 100 mM Tris buffer solution, a 100 to 200 mM sodium chloride (NaCl) solution, a 0.01 to 0.5% Triton X-100, and a protease inhibitor, and 1 to 10 mL, and more preferably, 3 to 8 mL per 1 g of a weight of the plant body is preferably used.

In the method of the present invention, a transformed plant body may be prepared by a method comprising: a) preparing a transformant by introducing the recombinant vector to a strain; and b) transforming a plant body using the transformant.

The strain may be *Agrobacterium tumefaciens*, but the present invention is not limited thereto. As the plant body, a dicotyledonous plant selected from the group consisting of *Arabidopsis thaliana*, soybean, tobacco, eggplant, pepper, potato, tomato, Chinese cabbage, radish, cabbage, lettuce, peach, pear, strawberry, watermelon, melon, cucumber, carrot and celery; or a monocotyledonous plant selected from the group consisting of rice, barley, wheat, rye, corn, sugarcane, oat and onion may be used. Still, the present invention is not limited thereto.

Hereinafter, to help in understanding the present invention, exemplary examples will be suggested. However, the following examples are merely provided to more easily understand the present invention and not to limit the present invention.

EXAMPLES

Example 1. Preparation of Transformed Plant Body Expressing the CBM3 Fusion Protein A vector for transforming a plant body, which is recombined to express a CBM3 fusion protein in the plant body. as shown in FIG. 1 was manufactured. To transfer the CBM3 fusion protein to the endoplasmic reticulum, a target protein was transferred to the endoplasmic reticulum using a genomic DNA sequence corresponding to a signal peptide of BiP, and His-Asp-Glu-Leu (HDEL) was introduced to a carboxyl end so that a fusion protein was accumulated in the endoplasmic reticulum and retained in the endoplasmic reticulum. CBM3 required for isolation of the fusion protein, a linker peptide (linker), and a sequence recognized and cleaved by enterokinase was connected upstream of a gene encoding the target protein (Ag85A), and inserted into a plant expression vector, i.e., pCAMBIA 1300, thereby preparing a recombinant vector. An *Agrobacterium tumefaciens* LBA-4404 strain was transformed with the vector. *Arabidopsis thaliana* was transformed using the modified *Agrobacterium* strain, thus developing a transformed plant body producing the target protein, and then the transformed plant body stably producing a CBM3 fusion protein was selected. The sequences used in the recombinant vector are shown in Table 1 below.

TABLE 1

| | Sequence (5'-3') | |
|---|---|---|
| CBM3 base sequence | gtatcaggtaaccttaaggtggagttttacaactcgaacccttctgatacaactaactc aataaacccacagttcaaagbacaaacacaggcagctctgcgatcgatttgtctaaatt aaccctcagatactattatacggttgatggacagaaggaccagactttcggtgtgatca tgcagctatcattggttctaacggtagctacaacggaattacatcaaacgtgaagggca ctttcgttaagatgtcctctagcactaacaacgcagacacatatttggagatcagtttt acgggggaacccttgaaccaggtgctcacgtccagattcaaggaagattcgctaaaaa cgactggtcgaactatacccaaagtaatgattacagtttaaatccgcctcacaatttg ttgagtgggatcaggtcactgcttacctgaacggggttctagtgtgggaaaggaacct ggt | SEQ ID NO: 1 |
| CBM3 amino acid sequence | VSGNLKVEFYNSNPSDTTNSINPQFKVTNTGSSAIDLSKLTLRYYYTVDGQKDQT FWCDHAAIIGSNGSYNGITSNVKGTFVKMSSSTNNADTYLEISFTGGTLEPGAHV QIQGRFAKNDWSNYTQSNDYSFKSASQFVEWDQVTAYLNGVLVWGKEPG | SEQ ID NO: 2 |
| Ag85A base sequence | tttagccggcctggcctgcctgtggaatacctgcaggtgcctagccctagcatgggccg ggacatcaaagtgcagtttcagagcggcggggctaatagccctgctctgtacctgctcg atggcctgcgggctcaggatgattttagcggctgggacatcaacacccctgcttttgaa tggtacgatcagagcggcctgagcgtcgtgatgcctgtgggcgggcagagcagcttcta cagcgattggtatcagctgcttgccgcaaagctggctgccagacctacaagtgggaaa cctttctgaccagcgaactgcctggctggctgcaggctaatcggcacgtgaaacctacc ggcagcgccgtggtgggcctgagcatggctgctagctccgctctgaccctggctatcta ccacccctcagcagtttgtgtacgctggcgctatgagcggcctgctcgatccctcccagg ctatgggccctaccctgatcgggctcgtatggggggatgctggggggtacaaagctagc gatatgtggggccctaaagaagatcctgcttggcagcggaatgatcctctgctcaacgt gggcaaactgatcgctaataatacccgagtgtgggtgtactgcggcaatggcaaaccta gcgatctgggcgggaacaatctgcctgctaaatttctggaaggcttcgtgcggaccagc aacatcaagtttcaggatgcttacaatgctggcgggggccacaatggcgtatttgattd cctgatagcggcacccacagctgggaatactggggcgctcagctgaatgctatgaaacc tgatctgcagcgggctctgggcgctaccccctaataccggccctgctcctcagggcgctg gctccggatctggtagt | SEQ ID NO: 3 |
| Ag85A amino acid sequence | FSRPGLPVEYLQVPSPSMGRDIKVQFQSGGANSPALYLLDGLRAQDDFSGWDINT PAFEWYDQSGLSVVMPVGGQSSFYSDWYQPACGKAGCQTYKWETFLTSELPGW LQANRHVKPTGSAVVGLSMAASSALTLAIYHPQQFVYAGAMSGLLDPSQAMGP TLIGLAMGDAGGYKASDMWGPKEDPAWQRNDPLLNVGKLIANNTRVWVYCGN GKPSDLGGNNLPAKFLEGFVRTSNIKFQDAYNAGGGHNGVFDFPDSGTHSWEY WGAQLNAMKPDLQRALGATPNTGPAPQGAGSGSGS | SEQ ID NO: 4 |
| Linker base sequence | gaggcagccgctaaggaagctgcagcgaaa | SEQ ID NO: 5 |

TABLE 1-continued

| | Sequence (5'-3') | |
|---|---|---|
| EK base sequence | gatgacgacgataaa | SEQ ID NO: 6 |
| BiP base sequence | atggctcgctcgtttggagctaacagtaccgttgtgttggcgatcatcttcttcggtga gtgattttccgatcttcttctccgatttagatctcctctacattgttgcttaatctcag aacctttttcgttgttcctggatctgaatgtgtttgtttgcaatttcacgatcttaaa aggttagatctcgattggtattgacgattggaatctttacgatttcaggatgtttattt gcgttgtcctctgcaatagaagaggctacgaagtta | SEQ ID NO: 7 |
| HDEL amino acid sequence | His-Asp-Glu-Leu | SEQ ID NO: 8 |

Example 2. Isolation of Protein Using MCC

To adsorb the CBM3 fusion protein to MCC, distilled water was added to 1 g of MCC to hydrate. Afterward, the transformed plant body prepared by the method described in Example 1 was cultured in the soil for about 3 weeks and then the plant body excluding the root part was ground in a mortar using liquid nitrogen. 1 g of the ground plant body was transferred to a new tube, 5 mL of a protein extraction buffer solution (50 mM Tris (pH 7.2), 150 mM NaCl, 0.2% Triton X-100, 1× protease inhibitor) was added thereto, and well mixed by vortexing. Plant debris was removed using Miracloth as a filter, 1 g of MCC was added, and then the resulting product was well mixed for 1 hour at 4° C., such that the CBM3 fusion protein was adsorbed to MCC. Afterward, proteins that were not bound to the MCC were removed through centrifugation (14,000 rpm, 4° C., 10 min), and then the MCC was washed with 5 mL of a washing buffer (50 mM Tris (pH 7.2), 150 mM NaCl) twice. The adsorption of the CBM3 fusion protein to the MCC was confirmed by western blotting using a CBM3 antibody.

Figure 2:
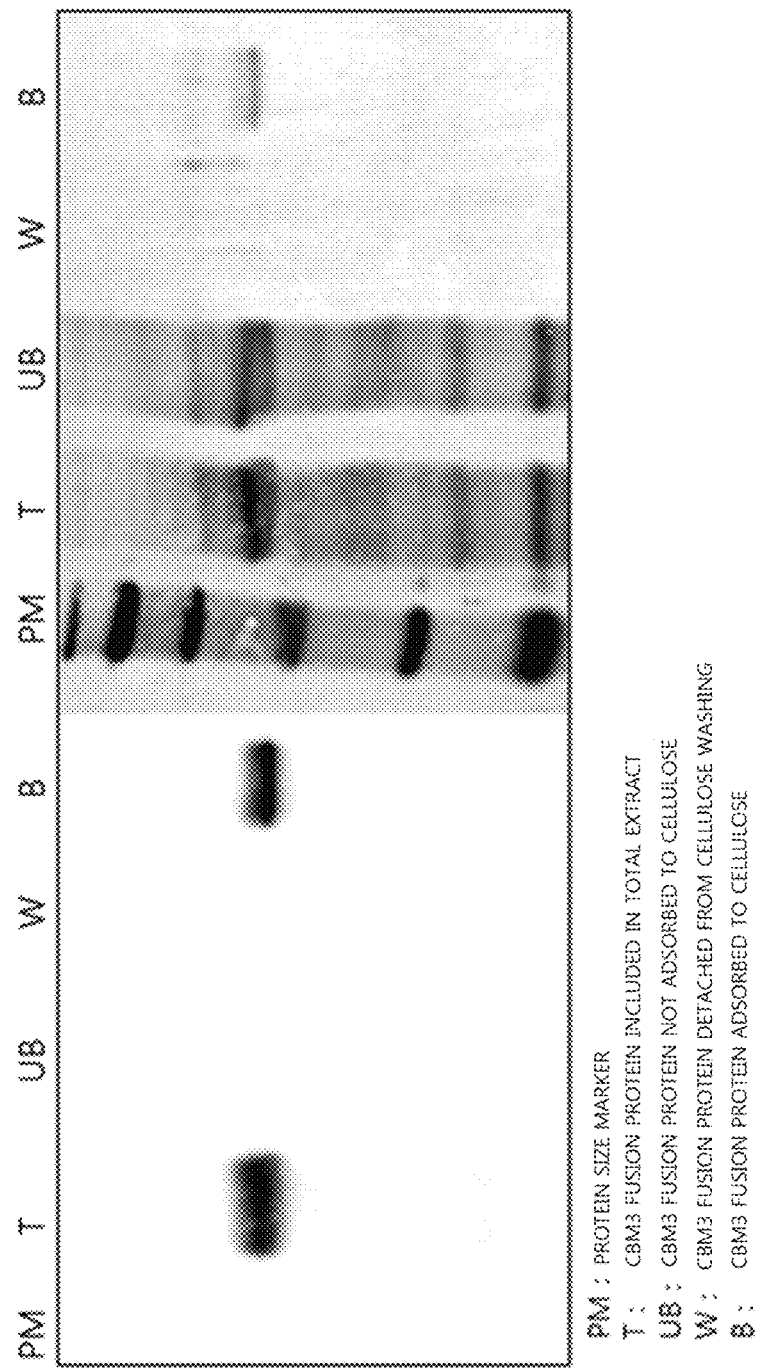
FIG. 2 illustrates the result obtained by confirming the adsorption of a CBM3 fusion protein (CBM3: Ag85A) to microcrystalline cellulose.

As a result, as shown in FIG. 2, it can be confirmed that the CBM3 fusion protein expressed in the plant was well adsorbed to the MCC with almost no loss, and the CBM3 fusion protein adsorbed to the MCC was hardly eluted even in the washing process.

Example 3. Cleavage of Fusion Protein Using Enterokinase

Ag85A-containing fusion protein-adsorbed cellulose was precipitated by centrifugation (14,000 rpm, 4° C., 10 min), and resuspended in an enterokinase reaction solution (50 mM Tris (pH 7.2), 150 mM NaCl, 1 mM CaCl$_2$)). As much as 5 units of enterokinase were added to the suspension and reacted at 28° C., a suspension was obtained hourly, and SDS-PAGE was performed. The cleavage of the fusion protein according to enterokinase treatment time was confirmed by western blotting using an Ag85A antibody.

Figure 3:
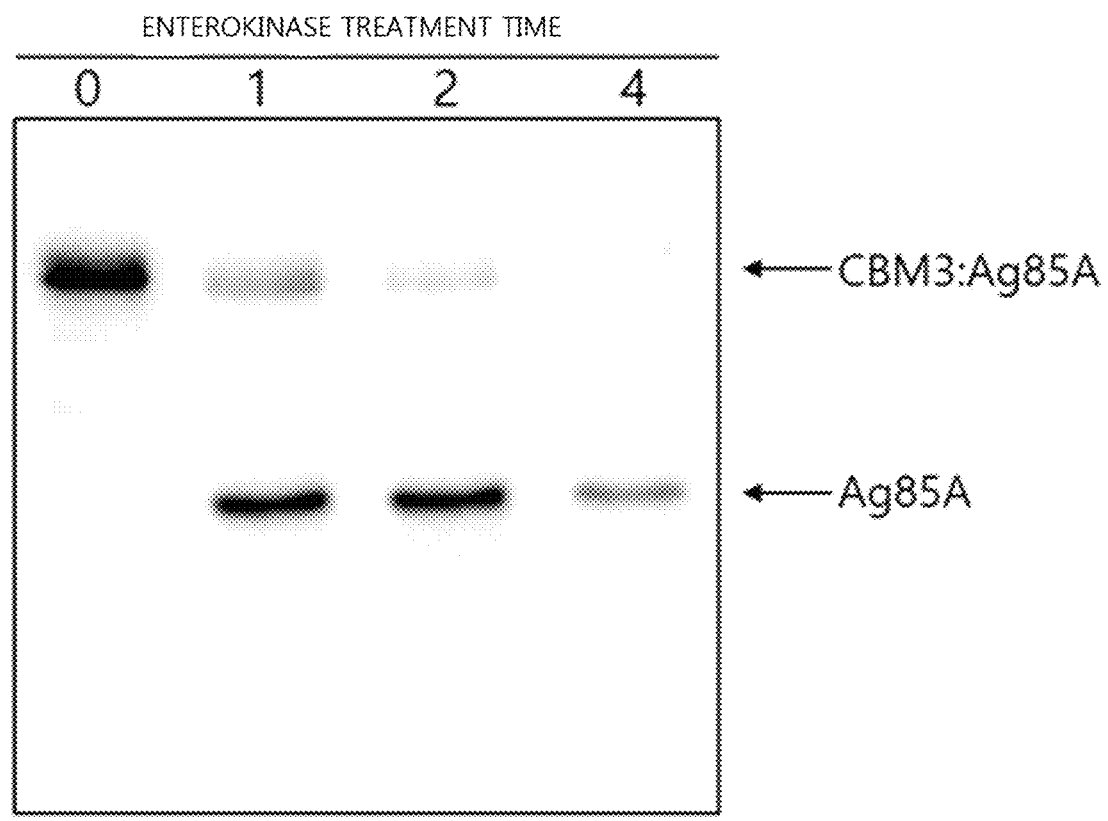
FIG. 3 illustrates the result obtained by isolating a target protein (Ag85A) from a CBM3 fusion protein using enterokinase.

As a result, as shown in FIG. 3, the cleavage reaction of the fusion protein by the enterokinase treatment was so efficient that 70% of the fusion protein was cleaved 1 hour after the treatment. After 4 hours, the fusion protein was completed cleaved and separated into CBM3 and Ag85A.

Figure 4:
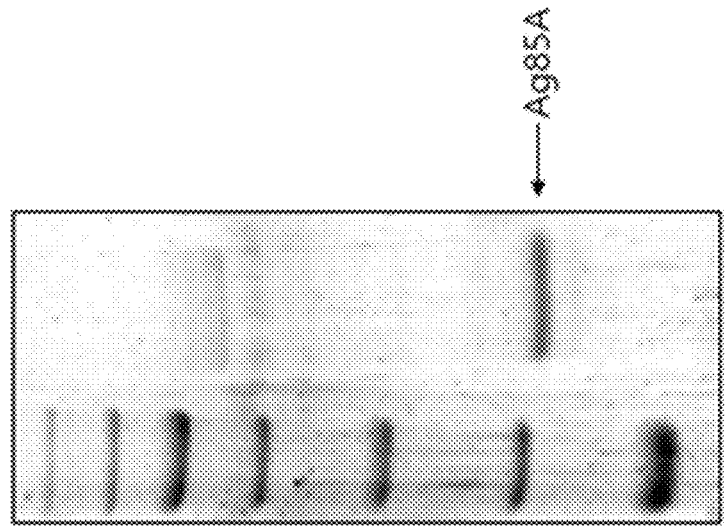
FIG. 4 illustrates the result obtained by isolating and purifying a target protein (Ag85A) after enterokinase is removed by affinity chromatography.
Figure 4:
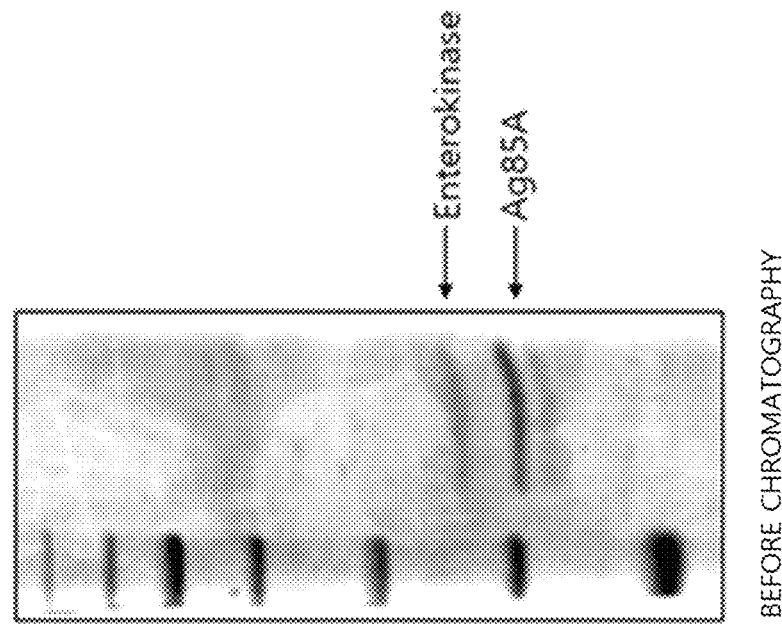

Example 4. Isolation and Purification of Ag85A by Removal of Enterokinase Through Affinity Chromatography The reaction solution containing the enterokinase and the completely-cleaved Ag85A was isolated from the cellulose through centrifugation (14,000 rpm, 4° C., 10 min) (left panel of FIG. 4). To remove enterokinase from the reaction solution, affinity chromatography was performed. STI-Sepharose was added to the reaction solution, reacted at 4° C. for 1 hour, and then put into an empty column to obtain a portion that did not bind to STI-Sepharose. As identified in the right panel of FIG. 4, it can be seen that enterokinase was removed from the reaction solution through STI-Sepharose affinity chromatography, thereby obtaining purified and isolated Ag85A.

From the above-described results, it was confirmed that the protein isolation method using a recombinant vector of the present invention might easily isolate enterokinase from a target protein without elution, such that the time to isolate a protein can be ultimately reduced. This means that, when a large amount of proteins is separated, due to the reduction in a sample used herein and time consumed, working efficiency can be maximized.

It should be understood by those of ordinary skill in the art that the above descriptions of the present invention are exemplary, and the example embodiments disclosed herein can be easily modified into other specific forms without changing the technical spirit or essential features of the present invention. Therefore, it should be understood that the example embodiments described above are exemplary in all aspects, and are not limitative.

INDUSTRIAL APPLICABILITY

A method of isolating a protein using a recombinant vector according to the present invention can rapidly, cheaply or efficiently separate a large amount of target proteins from a plant body with high purity, and thus is expected to be applied in various industrial fields.

The invention claimed is:

1. A recombinant vector comprising the polynucleotide sequence as set forth in SEQ ID NO: 1 encoding cellulose-binding module 3 (CBM3).

2. The recombinant vector, according to claim 1, wherein the recombinant vector comprises genes encoding cellulose-binding module 3, a linker peptide, an enterokinase-cleavage site, and a target protein, which is sequentially connected.

3. The recombinant vector, according to claim 2, wherein the target protein-encoding gene comprises of the polynucleotide sequence as set forth in SEQ ID NO: 3.

4. The recombinant vector according to claim 2, wherein the linker peptide is encoded by the polynucleotide as set forth in SEQ ID NO: 5.

5. The recombinant vector, according to claim 2, wherein the enterokinase-cleavage site is encoded by the polynucleotide as set forth in SEQ ID NO: 6.

6. The recombinant vector according to claim 2, further comprising a gene encoding binding immunoglobulin protein (BiP), wherein said BiP transfers a target protein to the endoplasmic reticulum in plant cells.

7. The recombinant vector according to claim 6, wherein the gene encoding the BiP is encoded by the polynucleotide as set forth in SEQ ID NO: 7.

8. The recombinant vector according to claim 2, further comprising a gene encoding a His-Asp-Glu-Leu (HDEL) peptide as set forth in SEQ ID NO: 8.

9. A method of isolating and purifying a target protein, comprising:
preparing a plant body mixed solution by mixing a plant body transformed using the recombinant vector of claim 1 with a protein extraction buffer solution (S1);
adsorbing a fusion protein, in which cellulose-binding module 3 and a target protein are fused, to cellulose by injecting the mixed solution of S1 into a column filled with cellulose (S2); and
obtaining a suspension by precipitating the fusion protein-adsorbed cellulose in S2 through centrifugation and suspending the precipitate in enterokinase (S3).

10. The method, according to claim 9, further comprising:
removing enterokinase by injecting the suspension into a sepharose column after S3.

11. The method according to claim 9, wherein the protein extraction buffer solution comprises a 10 to 100 mM Tris buffer, a 100 to 200 mM sodium chloride (NaCl) solution, a 0.01 to 0.5% Triton X-100 and a protease inhibitor.

12. The method according to claim 9, wherein the transformed plant body is prepared by a method comprising: a) preparing a transformant by introducing the recombinant vector of claim 1 to a strain, and b) transforming a plant body using the transformant.

13. The method, according to claim 12, wherein the strain is *Agrobacterium tumefaciens*.

14. The method, according to claim 9, wherein the plant body is a dicotyledonous plant selected from the group consisting of *Arabidopsis thaliana*, soybean, tobacco, eggplant, pepper, potato, tomato, Chinese cabbage, radish, cabbage, lettuce, peach, pear, strawberry, watermelon, melon, cucumber, carrot and celery; or a monocotyledonous plant selected from the group consisting of rice, barley, wheat, rye, corn, sugarcane, oat and onion.

15. The method, according to claim 9, wherein the cellulose is microcrystalline cellulose.

* * * * *